United States Patent
Leemrijse et al.

(10) Patent No.: US 10,022,170 B2
(45) Date of Patent: Jul. 17, 2018

(54) OSTEOTOMY DEVICE, IN PARTICULAR FOR PERFORMING EXTREME SCARF OSTEOTOMY IN THE TREATMENT OF SEVERE HALLUX VALGUS

(71) Applicant: BIOTECH ORTHO, Salon de Provence (FR)

(72) Inventors: Thibaut Leemrijse, Brussels (BE); Michel Maestro, Nice (FR); Bernhard Devos, Deurle (BE); Marc Relave, Andrezieu Boutheon (FR); Jean-Luc Besse, Chaponnay (FR)

(73) Assignee: TORNIER, Montbonnot-Saint-Martin (FR)

( * ) Notice: Subject to any disclaimer, the term of this patent is extended or adjusted under 35 U.S.C. 154(b) by 343 days.

(21) Appl. No.: 14/785,911

(22) PCT Filed: Apr. 2, 2014

(86) PCT No.: PCT/FR2014/050781
§ 371 (c)(1),
(2) Date: Dec. 28, 2015

(87) PCT Pub. No.: WO2014/177783
PCT Pub. Date: Nov. 6, 2014

(65) Prior Publication Data
US 2016/0074079 A1    Mar. 17, 2016

(30) Foreign Application Priority Data
Apr. 29, 2013   (FR) ...................................... 13 53917

(51) Int. Cl.
*A61B 17/80* (2006.01)
*A61B 17/86* (2006.01)

(52) U.S. Cl.
CPC ........ *A61B 17/809* (2013.01); *A61B 17/8047* (2013.01); *A61B 17/8057* (2013.01); *A61B 17/8061* (2013.01); *A61B 17/86* (2013.01)

(58) Field of Classification Search
CPC ... A61B 17/80; A61B 17/809; A61B 17/8057; A61B 17/8061
See application file for complete search history.

(56) References Cited

U.S. PATENT DOCUMENTS

| | | | |
|---|---|---|---|
| 7,309,340 B2* | 12/2007 | Fallin ................. | A61B 17/7059 606/104 |
| 2008/0046091 A1* | 2/2008 | Weiss ................... | A61B 17/686 623/22.37 |

(Continued)

FOREIGN PATENT DOCUMENTS

WO     2012112642 A1     8/2012

OTHER PUBLICATIONS

International Search Report for corresponding International Application No. PCT/FR2014/050781.

*Primary Examiner* — Christopher Beccia
(74) *Attorney, Agent, or Firm* — Duane Morris LLP

(57) ABSTRACT

An extreme movement osteotomy device includes an attachment plate suitable for being locked to the cortical substance of the bone to be treated, having a first proximal portion suitable for being attached to the inner cortical substance of the metatarsal diaphysis of the bone, a distal portion suitable for being attached to the outer cortical substance, next to the epiphysis of the metatarsus, and a central portion connecting the proximal and distal portions, each one of the proximal and distal portions of the plate being provided with at least one hole and orthopedic screws to pass therethrough; and a (Continued)

proximal intramedullary support system having a shank with a foam tip extending from the end of the proximal portion of the plate.

18 Claims, 4 Drawing Sheets

(56) References Cited

U.S. PATENT DOCUMENTS

2010/0256687 A1   10/2010  Neufeld et al.
2012/0209334 A1*   8/2012  Lewis ................ A61B 17/8014
                                                     606/286

* cited by examiner

OSTEOTOMY DEVICE, IN PARTICULAR FOR PERFORMING EXTREME SCARF OSTEOTOMY IN THE TREATMENT OF SEVERE HALLUX VALGUS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns an osteotomy device, in particular for the performance of SCARF osteotomy, well known to the practitioners, and especially for the performance of extreme SCARF (large displacement) in the treatment of severe Hallux Valgus.

However, this device is perfectly suitable for the performance of moderate SCARF, or also for the attachment of osteotomy of the first row on so-called extreme SCARF on the occasion of simple surgical reviews, or for example for osteoporotic patients for whom only the cortex (the cortical) is solid (even abnormally rigid).

2. Description of Related Art Including Information Disclosed Under 37 CFR 1.97 and 37 CFR 1.98

Hallux Valgus is a very widespread deformation of the foot corresponding to the deviation of the first metatarsal and the big toe of the first row. The inter-metatarsal angle I (between the metatarsals of the first and second rows) and the Hallux Valgus angle HV (between the metatarsus of the first row and the big toe) are radiographic measures commonly used to assess the degree of deformity of the metatarsus of the first row. These measures made it possible to establish the following classification: a Hallux Valgus is considered to be:

normal if: HV<15° and IM<9°
average if: 15°<HV<20° and 9°<IM<11°
moderate if: 20°<HV<40° and 11°<IM<16°
severe if: HV>40° and IM>16°

Several techniques exist to correct these deformities, with the intervention always occurring on the first metatarsus:
  osteotomy of the head of the first metatarsus (Reverdin Isham osteotomy) which allows redirecting the articular surface of the metatarsus and thereby correcting the deformity;
  Keller's operation corresponding to an arthroplasty by resection of the base of the first phalange of the big toe which remains in use in cases of arthrosic degeneration of the first metatarso-phalangeal joint;
  arthrodesis or metatarso-phalangeal "fusion" of the big toe.

The most common techniques remain however:
  diaphyseal osteotomy such as SCARF osteotomy;
  basal osteotomy such as chevron osteotomy or opening osteotomy with or without filling with graft.

It is possible to combine these interventions on the first metatarsus with the correction of the first phalange, for example by Akin osteotomy which corrects the valgus on the first phalange.

All these techniques provide good clinical and radiographic results. However, certain complications may occur such as the risk of thrombosis, of recurrence of Hallux Valgus, a "tile" effect (encasing of the two bone fragments), or metatarsalgia (pain in the forefoot, opposite the metatarsals).

The various studies undertaken in this field indicate that SCARF osteotomies provide an efficient method for the treatment of severe Hallux Valgus. However the devices currently available are not indicated for the correction of severe Hallux Valgus by the extreme SCARF technique.

In effect, for example, osteotomy plates are known which feature a first part intended to be applied to and fastened on the cortical substance of the bone to be treated, and a second part intended to be buried in the central medullary, in the diaphyseal portion of the bone to be treated.

For example, document WO-2012/112642 discloses an orthopedic plate with a first end featuring a locking screw hole intended for receiving a locking screw and, at a distance from this locking hole, a compression housing which extends from the face of the plate opposite the bone and which receives a compression screw the axis of which forms an angle between 10° and 70° with the longitudinal axis of the plate. This plate features also a second end with a chamfer to ensure the insertion of said plate into the bone.

This plate is especially indicated for corrections of Hallux Valgus through the CHEVRON technique. It is not appropriate for implementing the SCARF technique, and even less for extreme SCARF for treatment of severe Hallux Valgus.

Furthermore, the presence of the housing for the compression screw which extends from the lower face (intended to be applied opposite the bone to be treated), makes the device very complex to use.

One is also familiar with document US-2009/0036931 which discloses a plate for orthopedic surgery for osteosynthesis of bone fragments of the foot, this plate including a proximal portion intended to be placed and to be fastened on the external face of the first bone fragment, this proximal portion including at least one opening for passage of an orthopedic screw, and a distal portion intended to be placed in the central medullary housing of the second bone fragment, this distal portion likewise presenting at least one opening for passage of an orthopedic screw.

This plate is especially indicated for performing subcapital osteotomy or even for performing Lapidus arthrodesis.

Furthermore, its implementation, especially because of the need to screw orthopedic screws into the distal portion intended to be placed in the central medullary portion of the bone fragment, requires special instrumentation, as well as long and meticulous set-up time.

Even though this plate does not have a cumbersome, protruding housing, it is still not appropriate for application of the SCARF technique, and even less so for extreme SCARF for the treatment of severe Hallux Valgus.

In addition, each of the plates disclosed in documents WO-2012/112642 and US-2009/0036931 features a blade intended for insertion in the central medullary portion of the bone to be treated. This blade of a generally flat shape is cumbersome and difficult to insert into the spongy mass of the central medullary part and requires specific instrumentation adapted to its shape.

In addition, its end is slightly sharpened so as to be able to hollow out its seat in the central medullary part as the risk of damaging the internal cortical at said central medullary part.

These rigid blades cannot be shaped, or at least not in all directions.

One aim of the present invention is to offer practicing surgeons a device for extreme movement osteotomy, particularly for performing extreme SCARF in the treatment of severe Hallux Valgus that does away with the aforementioned disadvantages.

BRIEF SUMMARY OF THE INVENTION

According to the invention this aim has been achieved by a device for extreme movement osteotomy that is remarkable in that it includes:
an osteosynthesis attachment plate intended to be locked on the cortical substance of the bone to be treated, constituted by a first proximal portion suitable for being attached to the inner cortical substance of the metatarsal diaphysis of the bone, of a distal portion suitable for being attached to the outer cortical substance, in proximity of the epiphysis of the metatarsus, and of a central portion connecting said proximal and distal portions, each of the proximal and distal portions of the plate being provided with at least one hole for the passage of orthopedic screws;
a proximal central medullary holding system constituted by a shank with a foam tip extending from the end of the proximal portion of the plate.

According to an advantageous embodiment, the distal portion of the osteosynthesis plate includes two holes for the passage of orthopedic locking screws, the axes of which are perpendicular or approximately perpendicular to the plane of the plate and the proximal portion of the plate includes a hole for the passage of an orthopedic locking screw, the axis of which is perpendicular or approximately perpendicular to the plane of the plate and one hole for the passage of a non-locking orthopedic screw the axis of which is angular relative to the orthogonal at the plane of the plate.

According to an advantageous embodiment, the device according to the invention includes locking screws with a threaded head which may be self-tapping and the contours of the blocking holes for the passage of locking orthopedic screws are made of a material with mechanical properties permitting self-tapping by the threaded heads of the locking screws.

According to an advantageous embodiment, the contours of the blocking holes for the passage of orthopedic screws are made of polymers of the family of polyaryletherketones (PAEK), for example of polyetheretherketone (PEEK).

According to one embodiment, the contours of the holes for the passage of locked orthopedic screws are constituted by polymer inserts of the family of polyaryletherketones (PAEK), for example of polyetheretherketone (PEEK).

According to one implementation, the axis of the passage hole for the non-locking orthopedic screw located in the proximal portion of the place presents an angle between 0° and 45°, and preferably 20°.

According to an advantageous implementation, the central medullary shank is inclined relative to the plane in which the plate is included, for example by an angle between 0° and 30°, and preferably 10°.

According to another characteristic arrangement, the shank has a polygonal section, for example a square section with rounded angles.

According to an advantageous embodiment, the lower face of the plate which is to come into contact with the bone is granular (coated with corundum) in order to ensure better bone adhesion.

According to one embodiment, the plate and the shank of the osteotomy device are made of any biocompatible material with the necessary sturdiness, for example of pure titanium.

The osteotomy device according to the invention provides several interesting advantages, such as:
allowing strengthening of the self-locking base assembly of SCARF, due to the fact that little effort is applied to said device;
being adaptable to all situations since the central medullary shank can be slightly bent relative to the plate, so that the osteotomy device according to the invention is easily conformable to the morphology of the bone to be treated, and this in all directions, due to its shape as well as its material;
allowing a firm fit of the plate of the osteotomy device on the surface of the bone because of the use of locking screws;
allowing the addition of supplementary compression during the tightening of the unlocked (or adjusting) screw in order to bring the bone fragments together;
allowing the addition of supplementary rigidity and increased holding force because of the proximal shank positioned in the central medullary and resting on the inner cortical substance of the bone;
avoiding damage to the surface of the inner cortical substance of the bone thanks to the presence of the foam tip at the end of the shank.

Furthermore, this device can be used very reliably, its installation is easy, so it is a perfect match for the expectations of surgeons in terms of ease of installation and reliability in use.

BRIEF DESCRIPTION OF THE DRAWINGS

The abovementioned aims, characteristics and advantages, and still more, will become clearer in the detailed description below and in the attached drawings in which.

Figure 1:
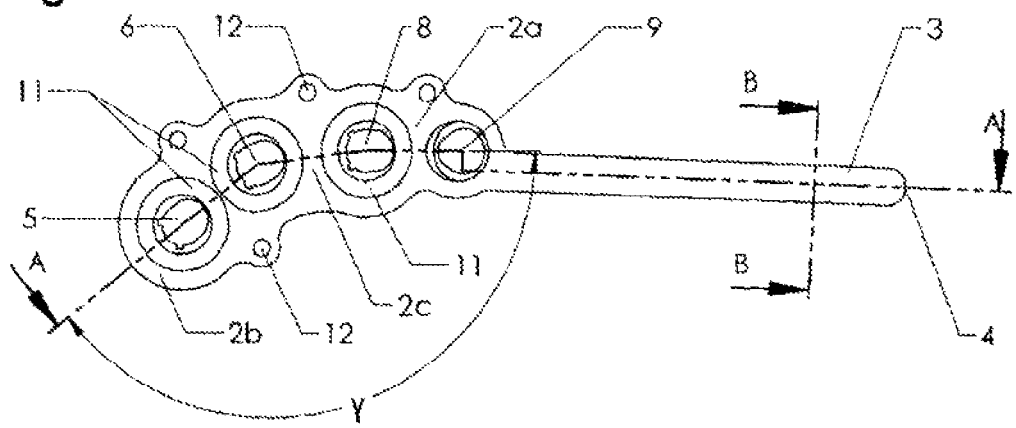
FIG. 1 is a plan view of a first example of embodiment of the osteotomy device according to the invention, a so-called 'small scale' [device] for use on the right foot.
Figure 2:
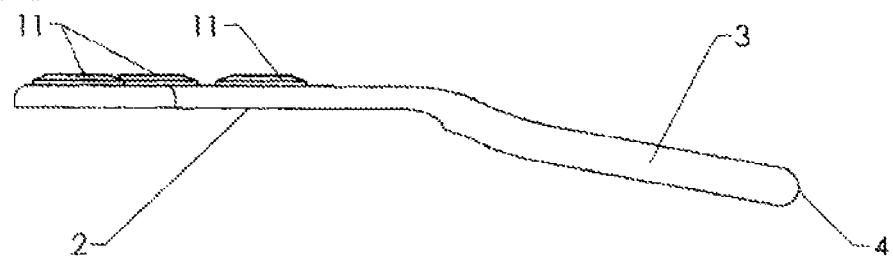
FIG. 2 is a side view of the osteotomy device according to FIG. 1.
Figure 3:
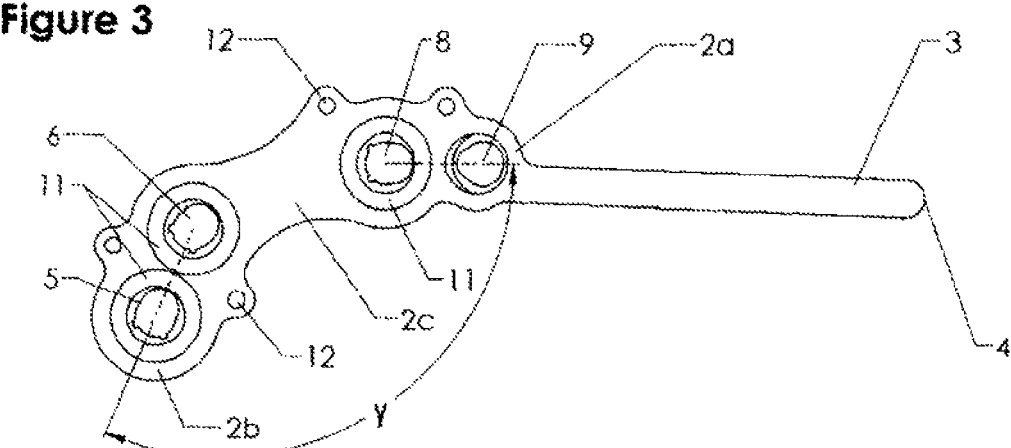
FIG. 3 is a plan view of a second example of embodiment of the osteotomy device according to the invention, a so-called 'large-scale' device for use on the right foot.
Figure 4:
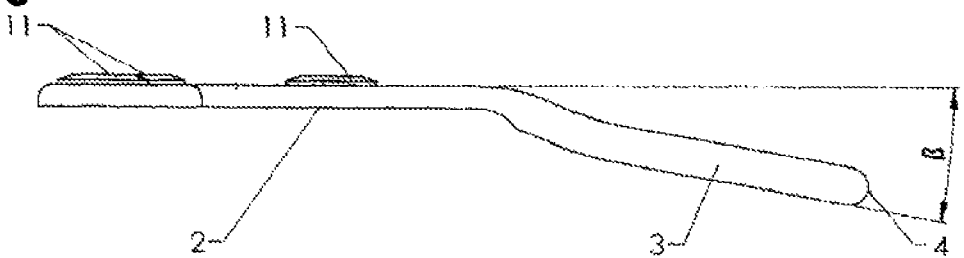
FIG. 4 is a side view of the osteotomy device according to FIG. 3.
Figure 5:
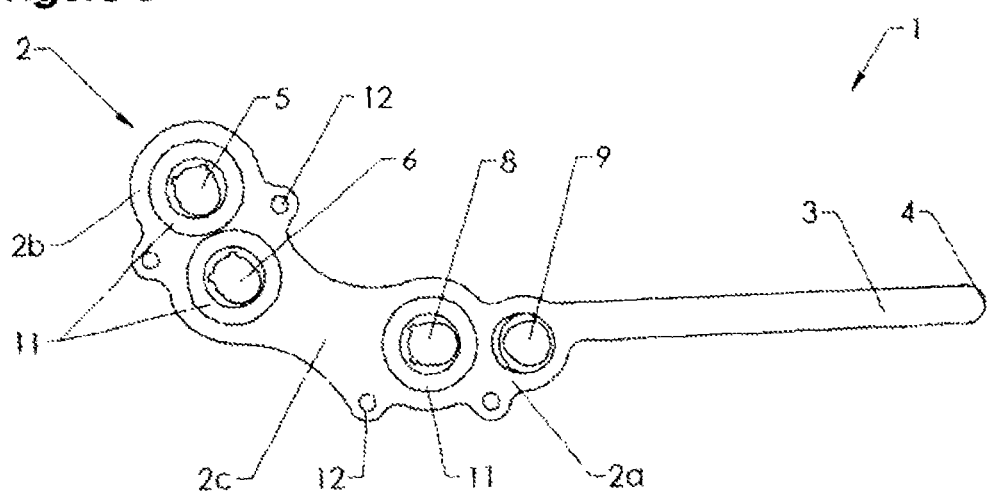
FIG. 5 is a plan view of a third example of embodiment of the osteotomy device according to the invention, a so-called 'large scale' device for use on the left foot.
Figure 6:
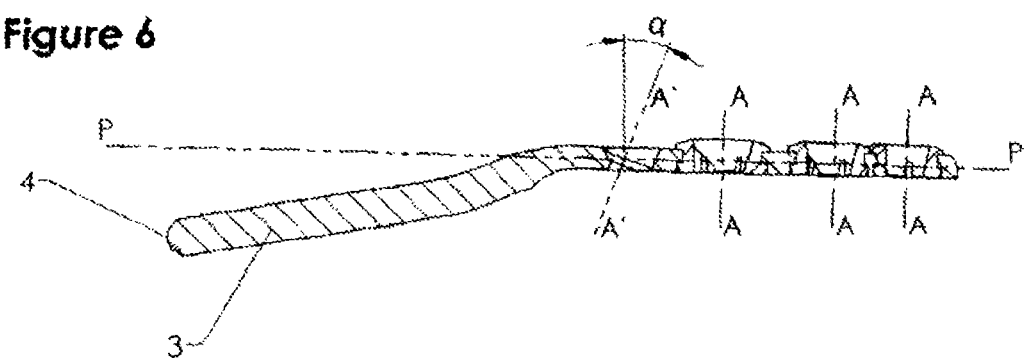
FIG. 6 is a sectional view along the line A-A of FIG. 1 of the osteotomy device according to the invention.
Figure 7:
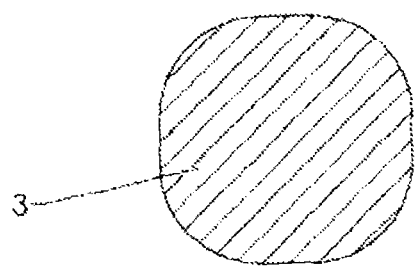
FIG. 7 is a sectional view along line B-B of FIG. 1 of the device according to the invention.
Figure 8:
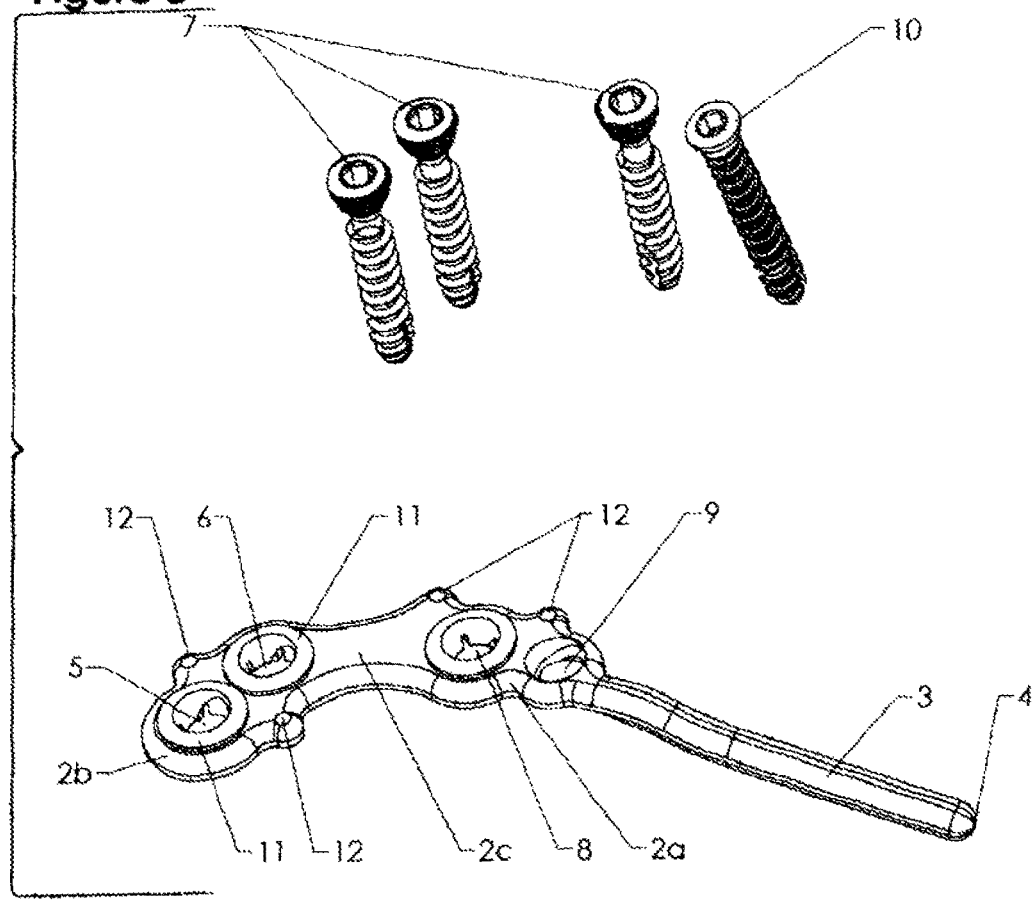
FIG. 8 is an exploded perspective view of the device and of orthopedic screws usable for fastening of said device.
Figure 9:
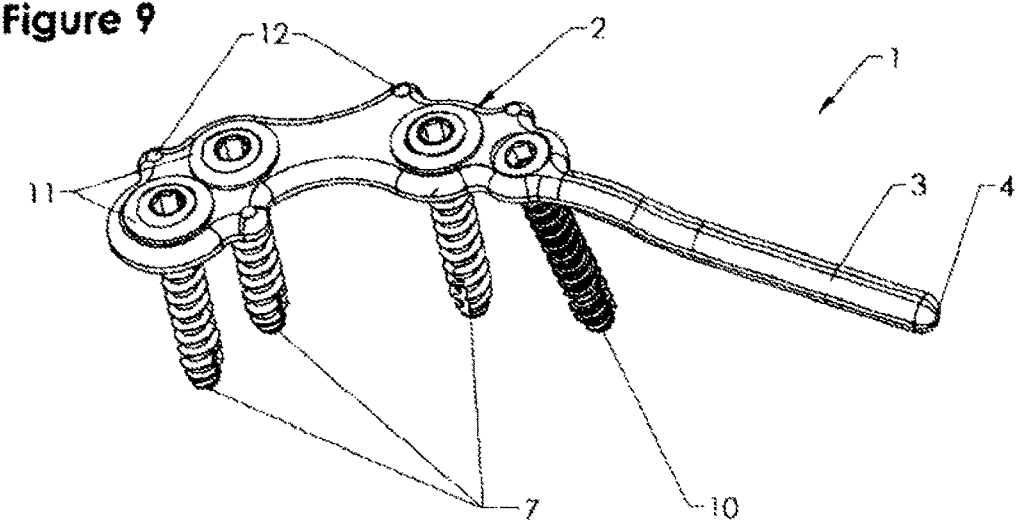
FIG. 9 is a view analog to FIG. 8 and shows the orthopedic screws in place in the device according to the invention.
Figure 10:
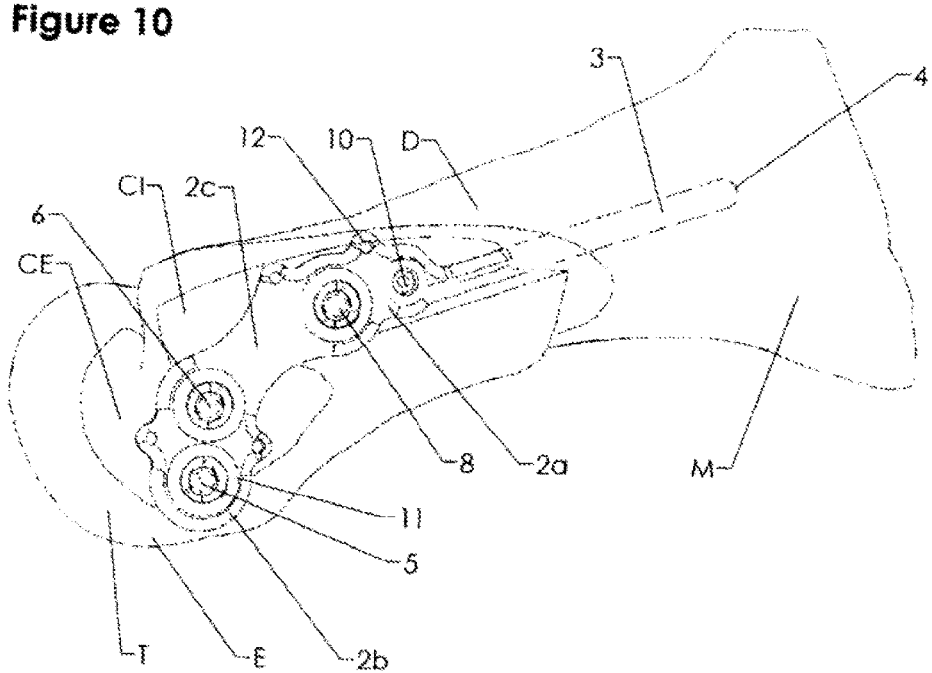
FIG. 10 is a perspective view illustrating the device according to the invention in place on a metatarsus.

Reference is made to said drawings to describe interesting, although by no means limiting, examples of embodiment of an extreme movement osteotomy device according to the invention.

DETAILED DESCRIPTION OF THE INVENTION

In the present disclosure document and in the claims, the words 'proximal' and 'distal' are used in reference to the functional positioning of the constitutive elements of the claimed device, the proximal portion being the closest to the heel of the foot whereas the distal portion is the closest to the toes of the foot.

Likewise, in the present disclosure document and in the claims, the inner face of the cortex (CI) corresponds to the interface between the spongy bone contained in the diaphysary part and the cortical bone.

The osteotomy device 1 according to the invention includes an osteosynthesis plate and orthopedic locking screws with threaded heads which may be self-tapping, and a non-locking orthopedic screw.

More precisely, the osteotomy device 1 according to the invention includes:
- an osteosynthesis attachment plate 2, capable of being locked on the cortical substance of the bone to be treated (namely the first metatarsus M) by means of orthopedic screws,
- a proximal central medullary holding system constituted by a shank 3 with a foam tip 4 positioned in the extension of the proximal portion of the plate.

The attachment plate 2 is advantageously constituted by:
- a proximal portion 2a, suitable for being attached on the inner cortex of the metatarsal diaphysis D of the bone,
- a distal portion 2b, suitable for being attached on the outer cortex, in proximity to the epiphysis E of the metatarsus,
- and a central portion 2c, connecting said proximal and distal portions.

The plate 2 has a general, inward-bent shape, for example the proximal portion of the plate and the distal portion of the plate form an angle γ between 90° and 180°. It presents a length of, for example, between 20 mm and 30 mm.

Devices of small dimensions may be offered (for example for use on a small metatarsus), featuring a plate in the order of 23 mm length, and large size devices (for example for use on a large metatarsus) featuring a plate in the order of 26 mm. In the case of so-called 'large size' devices, the surface of the central portion 2c is enlarged.

For example, for devices of the so-called 'small size', γ is in the order of 141°, while for so-called 'large size' devices, γ is in the order of 113°.

It may also have a width in the order of 7 mm and a thickness in the order of 1.2 mm.

Each of the proximal and distal portions, 2a and 2b respectively, of the plate 2 is provided with at least one hole for the passage of orthopedic screws.

According to the example shown, each of the proximal and distal portions, 2a and 2b respectively, of the plate 2 is provided with two holes for the passage of screws.

Preferably, the distal portion 2b includes two holes 5 and 6 for the passage of two locking screws. The axes A-A of holes 5 and 6 are perpendicular, or approximately perpendicular, to plane P-P of the plate 2, and the proximal portion 2a includes a hole 8 for the passage of a locking screw 7 the axis A-A of which is perpendicular, or approximately perpendicular, to the plane P-P of the plate and one hole 9 for the passage of a non-locking screw 10 the axis A'-A' of which is inclined by an angle α relative to the orthogonal on the plane P-P of the plate 2.

In a manner known as such, the locking screws 7 feature a threaded head of conical shape which may be self-tapping. These screws have, for example, a diameter in the order of 2.40 mm distally.

The non-locking screw 10 (also called the adjusting screw) known as such, presents, for example, a diameter in the order of 2.30 mm distally.

Advantageously, the axis A'-A' of the through-hole for the non-locking screw the proximal portion 2a of the plate 2 is provided with presents an angle α between 0° and 45°, and preferably 20°.

Advantageously, the shank 3 is inclined at an angle β relative to the plate 2. For example, this angle β is between 0° and 30°, and preferably, it is in the order of 10°.

This shank has a length in the order of 20 mm, so that the so-called 'small-size' devices present a total length of 43 mm and the so-called 'large size' devices have a total length of 46 mm.

Advantageously, the shank 3 has a polygonal section, for example and preferably, it is a square section with rounded angles, of about 2 mm per side, for example.

Preferably and advantageously the lower face of the plate 2 intended to be in contact with the bone is granular (coated with corundum) so as to ensure better bone adhesion. This bony adhesion enables the plate not to slide during the placement on the bone to be treated and thus ensures easy positioning of said plate. The granular aspect allows, once the plate is in place, better bone integration.

According to the manufacturing mode represented, the contours 11 of the locking holes 5, 6, and 8 for the passage of the locking screws 7 are executed in a material presenting mechanical properties permitting self-tapping by the threaded heads of the locked screws.

According to an advantageous implementation, the contours 11 of the locking holes 5, 6, and 8 for the passage of the locking screws 7 are made of polymers of the family of polyaryletherketones (PAEK), for example of polyetheretherketone (PEEK).

According to the example shown, the contours 11 of the locking holes 5, 6, and 8 for the passage of locking screws 7 are constituted by polymer inserts of the family of polyaryletherketones (PAEK), for example of polyetheretherketone (PEEK).

Locking of the heads of screws 7 in PEEK is inspired by the system described in Patent FR-2.845.588 "Self-blocking osteosynthesis devices" in the name of Biotech International and marketed under the registered brand name "EASY-LOCK".

The self-tapping head of locking screws 7 digs its own receiving helical groove in the contour 11 of the locking holes 5, 6, or 8 in which they are engaged, so that said screws then find themselves automatically blocked in the plate when their head is tightened in its seat.

On the other hand, this characteristic enables a selective angulation of the locking screws 7, relative to the axis A-A of said locking holes of the plate, depending on the needs, of ±10°.

The plate 2 also features several orifices 12 for the passage of fastening broaches allowing to firmly keeping the plate in place during its installation.

According to one embodiment, the plate and the shank of the osteotomy device are executed in any biocompatible material with the required sturdiness, for example they are made of pure titanium for maximum biocompatibility. Furthermore, this allows bending the shank 3 slightly relative to the osteosynthesis plate 2 (or inversely) and this in all directions, so as to make the osteotomy device conformable to the morphology of the bone to be treated.

The device according to the invention can thus be made available in a small size version, in the order of 43 mm length, or in the large size version in the order of 46 mm length, in the "right' version for use on a right foot, or in the 'left' version for use on a left foot.

The installation of the osteotomy device according to the invention by the SCARF method (well known by practitioners) consisting of obtaining a self-locking assembly involves the following steps:

1. perform the resection of the outer lateral head T of the metatarsus M;
2. perform the different cuts according to the SCARF method in the manner known as such;
3. select the osteotomy device 1 to be used depending on the morphology of the bones and the available surface (small or large device, left or right);
4. position the osteotomy device 1 by beginning to introduce the shank 3 for central medullary maintenance in the diaphyseal portion D of the proximal part of SCARF and, if necessary, slightly bend said shank 3 (or plate 2) so that the proximal portion 2a of the plate 2 rests on the inner surface of the cortical CI, and the distal portion 2b of the plate 2 rests on the outer surface of the cortex CE of said metatarsus;
5. maintain the plate in this position by means of broaches B passed through the holes 12;
6. use, in the manner known, a guide to prepare the bore and make sure not to damage the PEEK inserts as well as the angulated non-locking hole and bore said locations of the locking screws and of the non-locking screw;
7. use, in the manner known, a depth gauge in order to know the appropriate length of the screws to be used;
8. position the non-locking screw 10 and begin turning it but without tightening it all the way:
9. position the three locking screws 7 and fasten them, beginning with the distal hole 5;
10. complete fastening the non-locking screw 10.

The invention claimed is:
1. Osteotomy device comprising:
    plate suitable for being locked on the cortical substance of a metatarsus to be treated, the plate being constituted by:
        a proximal portion suitable for being attached on the inner cortical substance of the diaphysis of the metatarsus,
        a distal portion suitable for being attached to the outer cortical substance of the metatarsus, in proximity of the epiphysis of the metatarsus, and
        a central portion connecting said proximal and distal portions, each of the proximal and distal portions being provided with at least one hole for receiving an orthopedic screw, and
    a shank suitable for being positioned in the central medullary of the diaphysis of the metatarsus to hold the osteotomy device, the shank being provided with a foam tip,
    wherein the shank extends from a proximal end of the proximal portion and is integral with the plate so as to allow bending of the plate and the shank relative to each other.

2. Osteotomy device according to claim 1, wherein the distal portion of the plate includes two holes for receiving locking orthopedic screws, the two holes of the distal portion having respective axes which are perpendicular to a plane of the plate, and wherein the proximal portion of the plate includes:
    a first hole for receiving a locking orthopedic screw, the first hole of the proximal portion having an axis which is perpendicular to the plane of the plate, and
    a second hole for receiving a non-locking orthopedic screw, the second hole of the proximal portion having an axis which is angulated relative to an orthogonal on the plane of the plate.

3. Osteotomy device according to claim 1, wherein at least one of the holes of the plate has a contour which is made of a material having mechanical properties allowing self-tapping by a threaded head of a locking screw when received into said at least one of the holes.

4. Osteotomy device according to claim 3, wherein the osteotomy device includes at least one locking screw having a threaded head and wherein the contour of said at least one of the holes is made of a polymer of the family of polyaryletherketones (PAEK).

5. Osteotomy device according to claim 3, wherein the osteotomy device includes at least one locking screw having a threaded head and wherein the contour of said at least one of the holes is formed by an insert made of a polymer of the family of polyaryletherketones (PAEK).

6. Osteotomy device according to claim 1, wherein the at least one hole of the proximal portion has an axis which is angulated relative to an orthogonal on a plane of the plate, with an angle between 0° and 45°.

7. Osteotomy device according to claim 1, wherein the shank is inclined relative to a plane of the plate.

8. Osteotomy device according to claim 1, wherein the shank has a polygonal cross-section.

9. Osteotomy device according to claim 1, wherein a lower surface of the plate intended to be in contact with the metatarsus is granular so as to ensure better bone adhesion.

10. Osteotomy device according to claim 1, wherein the plate and the shank are made of a sturdy biocompatible material.

11. Osteotomy device according to claim 1, wherein the osteotomy device is designed for the performance of extreme SCARF in treatment of severe Hallux Valgus.

12. Osteotomy device according to claim 4, wherein the contour is made of polyetheretherketone (PEEK).

13. Osteotomy device according to claim 5, wherein the insert is made of polyetheretherketone (PEEK).

14. Osteotomy device according to claim 1, wherein the at least one hole of the proximal portion has an axis which is angulated relative to an orthogonal on a plane of the plate, with an angle of 20°.

15. Osteotomy device according to claim 7, wherein the shank is inclined relative to the plane of the plate with an angle between 0° and 30°.

16. Osteotomy device according to claim 7, wherein the shank is inclined relative to the plane of the plate with an angle of 10°.

17. Osteotomy device according to claim 8, wherein the shank has a square cross-section with rounded angles.

18. Osteotomy device according to claim 10, wherein the plate and the shank are made of pure titanium.

* * * * *